United States Patent [19]

Ryer et al.

[11] 4,153,566
[45] May 8, 1979

[54] OXAZOLINE ADDITIVES USEFUL IN OLEAGINOUS COMPOSITIONS

[75] Inventors: Jack Ryer, East Brunswick; Harold N. Miller, Millington; James Zielinski, Somerset, all of N.J.; Stanley J. Brois, Wantage, England

[73] Assignee: Exxon Research & Engineering Co., Florham Park, N.J.

[21] Appl. No.: 710,279

[22] Filed: Jul. 30, 1976

Related U.S. Application Data

[63] Continuation of Ser. No. 530,235, Dec. 6, 1974, abandoned, which is a continuation-in-part of Ser. No. 455,250, Mar. 27, 1974, abandoned.

[51] Int. Cl.$^2$ .............................................. C10M 1/32
[52] U.S. Cl. ........................... 252/51.5 A; 252/51.5 R; 260/307 F
[58] Field of Search ................... 252/51.5 R, 51.5 A; 260/307 F

[56] References Cited

U.S. PATENT DOCUMENTS

| | | | |
|---|---|---|---|
| 2,569,428 | 9/1951 | Rowland | 260/307 F |
| 2,831,858 | 4/1958 | de Benneville et al. | 260/307 F |
| 2,905,644 | 9/1959 | Butter | 260/307 F X |
| 3,219,666 | 11/1965 | Norman et al. | 252/51.5 A X |
| 3,235,557 | 2/1966 | Wiggins et al. | 260/307 F |
| 3,248,397 | 4/1966 | Purcell | 260/307 F |
| 3,966,620 | 6/1976 | Bridger et al. | 252/51.5 A |
| 4,035,309 | 7/1977 | Brois | 252/51.5 A X |
| 4,049,564 | 9/1977 | Ryer et al. | 252/51.5 A |

FOREIGN PATENT DOCUMENTS 1444904 2/1969 Fed. Rep. of Germany ..... 252/51.5 A

*Primary Examiner*—C. Davis
*Assistant Examiner*—Andrew Metz
*Attorney, Agent, or Firm*—Roland A. Dexter; Frank T. Johmann

[57] ABSTRACT

Oxazoline reaction products of hydrocarbon substituted dicarboxylic acid, ester, or anhydride, for example octadecenylsuccinic anhydride, with 2,2-disubstituted-2-amino-1-alkanols, such as tris-hydroxymethylaminomethane (THAM), and their derivatives are useful additives in oleaginous compositions, such as sludge dispersants for lubricating oil, or anti-rust agents for gasoline.

10 Claims, No Drawings

OXAZOLINE ADDITIVES USEFUL IN OLEAGINOUS COMPOSITIONS

CROSS-REFERENCE TO RELATED CASES

This is a continuation of application Ser. No. 530,235 filed Dec. 6, 1974 and now abandoned, which is a continuation-in-part of application Ser. No. 455,250 filed Mar. 27, 1974 now abandoned.

BACKGROUND OF THE INVENTION AND PRIOR ART

During the past decade, ashless sludge dispersants have become increasingly important, primarily in improving the performance of lubricants and gasoline in keeping the engine clean of deposits and permitting extended crankcase oil drain periods. Most commercial ashless dispersants fall into several general categories. In one category, an amine or polyamine is attached to a long chain hydrocarbon polymer, usually polyisobutylene, obtained by the reaction of halogenated olefin polymer with polyamine as in U.S. Pat. Nos. 3,275,554; 3,565,592; 3,565,804. In another category, a polyamine is linked to the polyisobutylene through an acid group, such as long chain monocarboxylic acid, e.g., see U.S. Pat. No. 3,444,170 or long chain dicarboxylic acid such as polyisobutenylsuccinic anhydride, by forming amide or imide linkages, such as described in U.S. Pat. Nos. 3,172,892; 3,219,666; etc. More recently, non-nitrogen ashless dispersants have been formed by esterifying long chain dicarboxylic acids; such as the polyisobutenylsuccinic anhydride, with polyols, such as pentaerythritol, as in U.S. Pat. No. 3,381,022.

Reaction products of hydrocarbon substituted succinic anhydride, e.g., the aforesaid polyisobutenylsuccinic anhydride, with compounds containing both an amine group and a hydroxy group have been suggested or investigated in the prior art. For example, U.S. Pat. No. 3,272,746 teaches the reaction of ethanolamine and diethanolamine, as well as various hydroxyalkyl substituted alkylene amines, such as N-(2-hydroxyethyl) ethylene diamine, N,N'-bis(2-hydroxyethyl) ethylene diamine, with alkenyl succinic anhydride to obtain ashless dispersants for lube oil. A hydroxy amine, such as diethanolamine, is reacted with a long chain alkenylsuccinic anhydride in U.S. Pat. No. 3,324,033 to form a mixture of esters and amides, wherein some of the diethanolamine reacts through a hydroxy group to give an ester linkage, which another portion of the diethanolamine forms an amide linkage. U.S. Pat. No. 3,364,001 teaches a tertiary alkanolamine reacted with an alkenyl succinic anhydride to form an ester useful as a gasoline additive. U.S. Pat. No. 3,448,049 teaches dispersants, corrosion inhibitors and antiwear agents in lubricants and fuels by esterifying alkenyl succinic anhydride with a hydroxy compound made by reacting an alkanolamine with an unsaturated ester, amide or nitrile. U.S. Pat. No. 3,630,904 teaches reacting a hydroxy amine, with both short and long chain dicarboxylic acid. U.S. Pat. No. 3,484,374 teaches the polymeric condensation products of polycarboxylic acid or anhydride with various alkanolamines such as aminoethylethanolamine, N-methyldiethanolamine, etc. United Kingdom Specification 809,001 teaches corrosion inhibitors comprising a multiple salt complex derived from the reaction product of hydrocarbyl substituted dicarboxylic acids and hydroxy amines (including 2-amino-2-methyl-1,3-propanediol [AMP] and tris hydroxymethylaminomethane [THAM]) further complexed with mono- and polycarboxylic acids (see Examples 17–19).

U.S. Pat. No. 3,576,743 teaches reacting polyisobutenylsuccinic anhydride with a polyol, such as pentaerythritol, followed by reaction with THAM, (see Example 1). U.S. Pat. No. 3,632,511 teaches reacting polyisobutenylsuccinic anhydride with both a polyamine and a polyhydric alcohol including THAM. U.S. Pat. No. 3,697,428 (Example 11) teaches reacting polyisobutenylsuccinic anhydride with a mixture of pentaerythritol and THAM. United Kingdom Specification No. 984,409 teaches ashless, amide/imide/ester type lubricant additives prepared by reacting an alkenyl succinic anhydride, said alkenyl group having 30 to 700 carbon atoms, with a hydroxy amine including THAM.

SUMMARY OF THE INVENTION

As noted above, the prior art teaches dispersants formed from hydrocarbyl substituted dicarboxylic acid material, usually alkenyl succinic anhydride, reacted with various amine or hydroxy compounds either through an amide, imide or ester linkage. In contrast to most of the prior art, the present invention is based upon the discovery that reaction of hydrocarbyl dicarboxylic acid material, i.e. acid or anhydride or ester, with certain classes of amino alcohols, under certain conditions, will result in a heterocyclic ring structure, namely an oxazoline ring, and that materials with this oxazoline ring including derivatives thereof can be tailored for various functions, such as anti-rust agents, detergents, or dispersants for oleaginous compositions including lube oil, gasoline, turbine oils and oils for drilling applications.

The compounds of the invention have at least 8 carbons in the substantially saturated aliphatic hydrocarbyl group and at least one carboxylic acid group converted into an oxazoline ring as a result of the reaction of at least equimolar amounts of said hydrocarbon substituted $C_4$–$C_{10}$ mono-unsaturated dicarboxylic acid material and a 2,2-disubstituted-2-amino-1-alkanol having 2 to 3 hydroxy groups and containing a total of 4 to 8 carbons.

THE HYDROCARBYL DICARBOXYLIC ACID MATERIAL

The hydrocarbyl substituted dicarboxylic acid material, i.e., acid or anhydride, or ester, used in the invention includes alpha-beta unsaturated $C_4$ to $C_{10}$ dicarboxylic acid, or anhydrides or esters thereof, such as fumaric acid, itaconic acid, maleic acid, maleic anhydride, chloromaleic acid, dimethyl fumarate, etc., which are substituted with a hydrocarbon chain containing at least 8 carbons, preferably from 8 to 49 or 50 carbons (branched or unbranched).

In general, these hydrocarbyl substituted dicarboxylic acid materials and their preparation are well known in the art as well as several being commercially available, e.g., 2-octadecenylsuccinic anhydride.

The hydrocarbyl portion optionally should average from about 16 to about 50 aliphatic carbon atoms per dicarboxylic acid group and be substantially saturated. Further examples of the hydrocarbyl substituent portion are set forth in U.S. Pat. No. 3,458,444 which shows such dicarboxylic acids reacted with tertiary amines to produce rust and sludge inhibitors.

Frequently these hydrocarbyl substituted dicarboxylic acid materials are prepared by reacting the unsaturated dicarboxylic acid material, usually maleic anhydride, with a 1-olefin, e.g. an olefin polymer of from about 30 to about 50 carbons still retaining a terminal unsaturation.

THE AMINO ALCOHOL

The amino alcohol used to make the oxazoline dispersant is a 2,2-disubstituted-2-amino-1-alkanol, having 2 to 3 hydroxy groups, containing a total of 4 to 8 carbon atoms, and which can be represented by the formula:

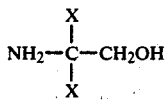

wherein X is an alkyl, or hydroxy alkyl group, with at least one of the X substituents, and preferably both of the X substituents, being a hydroxy alkyl group of the structure $-(CH_2)_nOH$, wherein n is 1 to 3.

Examples of such 2,2-disubstituted amino alkanols, include 2-amino-2-methyl-1,3-propanediol, 2-amino-2-(hydroxymethyl)-1,3-propanediol (also known as tris-hydroxyaminomethane or THAM), 2-amino-2-ethyl-1,3-propanediol, etc. Because of its effectiveness, availability, and cost, the THAM is particularly preferred.

THE OXAZOLINE REACTION CONDITIONS

The formation of the novel oxazoline materials, in a fairly higher yield, can be effected by adding about 1 to 2 mole equivalent of the aforesaid 2,2-disubstituted-2-amino-1-alkanol per mole equivalent of the dicarboxylic acid material, with or without an inert diluent, and heating the mixture at 140°–240° C., preferably 170°–220° C. for ½ to 24, more usually 2 to 8 hours.

Although not necessary, the presence of small amounts, such as 0.01 to 2 wt. %, preferably 0.1 to 1 wt. %, based on the weight of the reactants, of a metal salt can be used in the reaction mixture as catalyst to shorten the reaction times. The metal catalyst can later be removed by filtration or by washing a hydrocarbon solution of the product with a lower alcohol, such as methanol, ethanol, isopropanol, etc., or an alcohol/water solution.

Alternatively, the metal salt can be left in the reaction mixture, as it appears to become stably dispersed, or dissolved, in the reaction product, and depending on the metal, it may even contribute performance benefits to the oil or gasoline. This is believed to occur with the use of zinc catalysts in lubricants.

Inert solvents which may be used in the above reaction include hydrocarbon oils, e.g., mineral lubricating oil, kerosene, neutral mineral oils, xylene, halogenated hydrocarbons, e.g., carbon tetrachloride, dichlorobenzene, tetrahydrofuran, etc.

Metal salts that may be used as catalysts in the invention include carboxylic acid salts of Zn, Co, Mn and Fe. Metal catalysts derived from strong acids (HCl, sulfonic acid, $H_2SO_4$, $HNO_3$, etc.) and bases, tend to diminish the yield of the oxazoline products and instead favor imide or ester formation. For this reason, these strong acid catalysts or basic catalysts are not preferred and usually will be avoided. The carboxylic acids used to prepare the desired catalysts, include $C_1$ to $C_{18}$, e.g., $C_1$ to $C_8$, acids, such as the saturated or unsaturated mono and dicarboxylic aliphatic hydrocarbon acids, particularly fatty acids. Specific examples of such desired carboxylic acid salts include zinc acetate, zinc formate, zinc propionate, zinc stearate, manganese (ous) acetate, iron tartrate, cobalt (ous) acetate, etc. Completion of the oxazoline reaction can be readily ascertained by using periodic infrared spectral analysis for following the oxazoline formation (oxazoline peak forms at 6.0 microns), or by the cessation of water evolution.

REACTION MECHANISM OF THE OXAZOLINE FORMATION

While not known with complete certainty, but based on experimental evidence, it is believed that the reaction of the hydrocarbyl substituted dicarboxylic acid material, e.g., a substituted succinic anhydride, with the amino alcohol of the invention, e.g., two equivalents of 2,2-disubstituted-2-aminoethanol such as tris-hydroxymethylaminomethane (THAM), gives oxazoline, e.g., bis-oxazolines, via the intermediacy of several discrete reaction species. If an acid anhydride is used, the initial transformation appears to involve the scission of the anhydride by the amino function of one mole of the amino alcohol to yield an amic acid. Addition of another mole equivalent of amino alcohol is believed to form the amic acid amine salt, which then upon further heating, undergoes cyclo-dehydration to the final bis-oxazoline product. The catalyst effect of metal salts, such as zinc acetate ($ZnAc_2$), on oxazoline formation is very likely ascribable to the favorable polarization of the amide group by the zinc ion towards attack by the hydroxy function of the amino alcohol reactant. These reactions can be typified as follows in the case of bis-oxazoline:

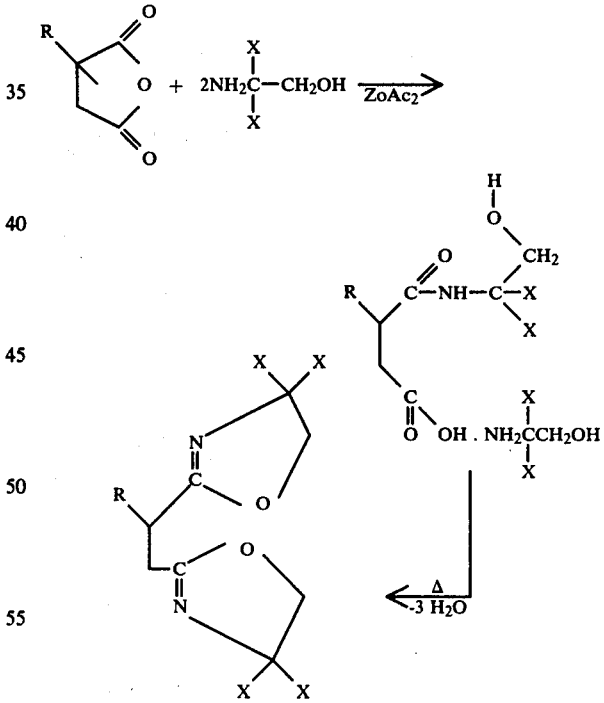

where R is the hydrocarbyl group of the succinic anhydride, and each X in this case of using tris-hydroxymethylaminomethane (THAM) represents a $-CH_2OH$ group.

In contrast to the above oxazoline formation using the disubstituted amino alcohol, if the amino alcohol has no substituents as in 2-aminoethanol, or has only one substituent in the 1- or 2-position as in 2-amino-1-propanol, 2-amino-1-butanol, and related mono-substituted 2-aminoethanols, the aminoalcohol fails to undergo the aforesaid oxazoline reaction. Instead, these other amino alcohols will react with the succinic anhydride to give almost exclusively succinimide products as illustrated in the following reaction.

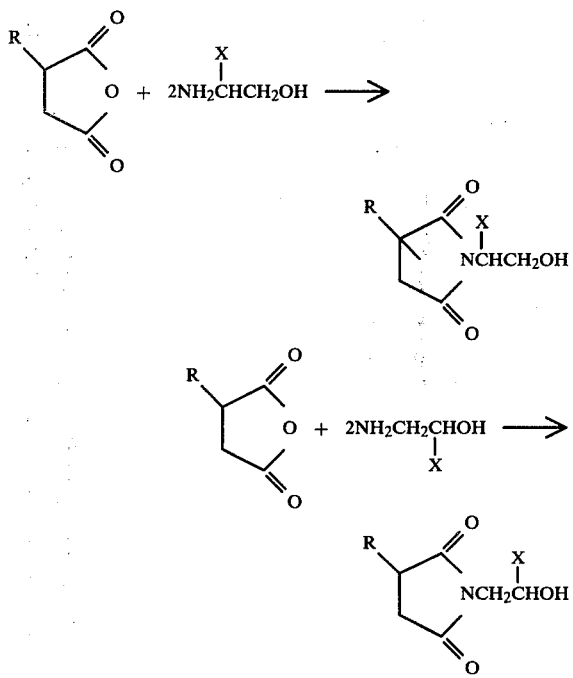

wherein R and X are as previously defined. In no instances were discernible amounts of bis-oxazoline products found in experiments on the above reactions.

Condensation of about 1 mole equivalent of the aforesaid 2,2-disubstituted amino alcohol with about one mole equivalent of said dicarboxylic acid material affords the mono-oxazoline ester.

USE OF THE OXAZOLINE ADDITIVE IN OLEAGINOUS COMPOSITIONS

The oil soluble oxazoline reaction products of this invention can be incorporated in a wide variety of oleaginous compositions. They can be used in lubricating oil compositions, such as automotive crankcase lubricating oils, automatic transmission fluids, etc. in concentrations generally within the range of about 0.01 to 20 weight percent, e.g., 0.1 to 10 weight percent, preferably 0.3 to 3.0 weight percent, of the total composition. The lubricants to which the oxazoline products can be added include not only hydrocarbon oils derived from petroleum, but also include synthetic lubricating oils such as polyethylene oils; alkyl esters of dicarboxylic acid; complex esters of dicarboxylic acid, polyglycol and alcohol; alkyl esters of carbonic or phosphoric acids; polysilicones; fluorohydrocarbon oils; mixtures of mineral lubricating oil and synthetic oils in any proportion, etc.

When the products of this invention are used as multi-functional additives having detergents, anti-rust properties in petroleum fuels such as gasoline, kerosene, diesel fuels, No. 2 fuel oil and other middle distillates, a concentration of the additive in the fuel in the range of 0.001 to 0.5 weight percent, based on the weight of the total composition, will usually be employed.

When used as an antifoulant in oil streams in refinery operations to prevent fouling of process equipment such as heat exchangers or in turbine oils, about 0.001 to 2 wt. % will generally be used.

The additive may be conveniently dispensed as a concentrate comprising a minor proportion of the additive, e.g., 2 to 45 parts by weight, dissolved in a major proportion of a mineral lubricating oil, e.g., 98 to 45 parts by weight, with or without other additives being present.

In the above compositions or concentrates, other conventional additives may also be present including dyes, pour point depressants, antiwear agents such as tricresyl phosphate or zinc dialkyldithiophosphates of 3 to 8 carbon atoms in each alkyl group, antioxidants, such as N-phenyl α-naphthylamine, tert-octylphenol sulfide, 4,4'-methylene bis(2,6-di-tert-butyl phenol), viscosity index improvers such as ethylene-propylene copolymers, polymethacrylates, polyisobutylene, alkyl fumarate-vinyl acetate copolymers and the like, deemulsifiers such as polysiloxanes, ethoxylated polymers and the like.

This invention will be further understood by reference to the following examples, which include preferred embodiments of the invention.

EXAMPLE 1

A bis oxazoline of octadecenylsuccinic anhydride and 2-amino-2-methyl-1-propanol (AMP) was prepared as follows:

A mixture of 527 gm. (1.5 moles) of 2-octadecenylsuccinic anhydride, commercially available from Humphrey Chemical or Monsanto, St. Louis, Mo., 200 ml. of tetrahydrofuran (THF) as solvent, 4 gm. of zinc acetate dihydrate ($ZnAc_2.2H_2O$) as a catalyst and 267 gm. (3.0 mole) of 2-amino2-methyl-1-propanol (AMP) was charged into a laboratory glass 1 liter reaction flask, equipped with a bottom draw-off, a thermometer, a charging funnel, a nitrogen bleed, and an overhead condenser equipped with a Deane-Starke water trap. The flask was heated in an oil bath. When the reaction temperature had risen to 72° C., the THF solvent distilled off. Further heating at about 200° C. for several hours gave the expected quantity of water, i.e., about 81 grams of water in the trap. Vacuum distillation of the crude mixture produced an amber liquid as residue which boiled at 245°–251° C. (ca. 1 mm Hg). Infrared and NMR spectral data of said residue confirmed the bis-oxazoline structure. Analysis gave the following: 75.60 wt. % carbon (calculated 75.89 wt. %); 11.53 wt. % hydrogen (calculated 11.46 wt. %); 5.38 wt. % nitrogen (calculated 5.89 wt. %); and 7.12 wt. % oxygen (calculated 6.76 wt. %). The calculated amounts were based on $C_{30}H_{54}N_2O_2$.

EXAMPLE 2

A mixture of 21 gm. (0.1 mole) of diisobutenyl-succinic anhydride in 100 ml. of THF was reacted with tris-hydroxymethylaminomethane by the portionwise addition of 24.2 gms. (0.2 mole) of the latter to the mixture in the glass reactor, previously described, at about 35° C. After evaporation of the THF solvent, the mixture was heated in the oil bath at about 200°–220° C. for about two hours. The infrared spectrum of the reaction product drawn from the flask showed a strong absorption band at 6.0 microns showing the oxazoline structure had formed. Analysis showed that the final product contained 58.07 wt. % carbon; 8.60 wt. % hydrogen, and 7.00 wt. % nitrogen.

EXAMPLE 3

178 grams (2.0 moles) of 2-amino-2-methyl-1-propanol (AMP) were gradually added to 210 gm. (1.0 mole) of 2-octenyl succinic anhydride. The reaction temperature peaked to 130° C. during the AMP addition. The mixture was thereafter heated to 196° C. for three hours, followed by addition of 28 gm. of AMP and subsequent heating for 6 hours at 194° C.

EXAMPLE 4

210 gm. (1.0 mole) of 2-octenylsuccinic anhydride was gradually added to 267 gm. (3.0 1 moles) of AMP containing 4.0 gm. of zinc acetate dihydrate. The reaction mixture was refluxed for several hours. During this period, excess amino alcohol and water was collected using a distilling head mounted on the reactor. The reaction was stopped when water ceased to distil over. Distillation of the crude product afforded a clear liquid which boiled at 171°–173° C. (0.15 mm Hg). The infrared spectrum of the bis-oxazoline product exhibited a strong absorption band at about 6 microns. Analysis of the reaction product gave 71.11 wt. % carbon (calculated 71.59 wt. %); 10.28 wt. % hydrogen (calculated 10.52 wt. %); and 8.25 wt. % nitrogen (calculated 8.35 wt. %). The calculated figures were based on $C_{20}H_{35}N_2O_2$.

EXAMPLE 5

A mono-oxazoline of octadecenyl succinic anhydride and tris-hydroxymethylaminomethane was prepared as follows:

A mixture of 87.8 gm. (0.25 mole) of 2-octadecenyl succinic anhydride and 30.75 gm. (0.25 mole) of tris-hydroxymethylaminomethane and 0.5 gm. of zinc acetate dihydrate were mixed together and gradually heated to 210° C. in the apparatus of Example 1. The reaction was continued at this temperature until the evolution of water ceased. A sample of the product was recrystallized from acetone/hexane solution and submitted to elemental analysis which showed 71.00 wt. % carbon (calculated 71.68 wt. %); 10.33 wt. % hydrogen (calculated 10.41 wt. %); and 4.12 wt. % nitrogen (calculated 3.22 wt. %). The calculation was based on $C_{26}H_{45}NO_4$. The infrared spectrum of the product featured strong ester and oxazoline absorption and at 5.75 and 6.0 microns, respectively. The molecular weight of the product by osmometry was found to be 2324.

EXAMPLE 6

21 gm. (0.1 mole) of diisobutenylsuccinic anhydride was mixed with 12 gms. (0.1 mole) of tris-hydroxymethylaminomethane in the presence of 0.5 gm. of zinc acetate dihydrate and heated to about 140° C. At this temperature, water began to distill from the reactor. Heating was gradually increased to about 180°–190° C. over a four hour period during which 36 milliliters of water were collected. The infrared spectrum of the reaction mixture revealed the presence of mono-oxazoline product in high yield.

EXAMPLE 7

584 gm. (1.5 moles) of 90% active 2-octadecenyl-succinic anhyride and 4.0 gm. of zinc acetate dihydrate was slurried in 200 ml. of tetrahydrofuran. To this was added 363 gms. (3.0 moles) of 2-amino-2-(hydroxymethyl)-1,3-propanediol. The temperature was gradually raised to 160° C. effectively removing most of the solvent. Following this the mixture was heated to 208° C. over a three-hour period during which water distilled. The contents were found to have a prominent absorption band at about 6.0 microns. Recrystallization of the crude reaction product gave a white solid which melted at 104°–106° C. The recrystallized product showed the following analysis: 66.80 wt. % carbon (calculated 66.83 wt. %); 9.86 wt. % hydrogen (calculated 10.10 wt. %); 4.59 wt. % nitrogen (calculated 5.20 wt. %); and 18.40 wt. % oxygen (calculated 17.82 wt. %). Calculated values were based on $C_{30}H_{54}N_2O_6$.

The product of Example 7 was tested for its effectiveness as a gasoline anti-rust agent. This product was first dissolved in xylene, and the solution was added to the gasoline to incorporate the additive at a treat rate of 10 pounds of oxazoline additive per thousand barrels of gasoline, i.e., about 0.024 wt. %. The gasoline so treated was then tested for rust according to ASTM D-665M rust test. In brief, this test is carried out by observing the amount of rust that forms on a steel spindle after rotating for an hour in a water-gasoline mixture. In this case, the oxazoline treated gasoline gave no rust indicating that it was very effective as an antirust additive since the untreated gasoline will give rust over the entire surface of the spindle.

In other identical testing (except that the treat rate was 6.25 lbs. of additive product per 1000 barrels of gasoline), the reaction product of Example 5 was found to be very effective as an anti-rust additive for gasoline.

The oxazoline reaction products of the invention which are primarily useful as an anti-rust additive and/or detergent for gasoline will generally have hydrocarbyl substituents numbering from about 12 to about 49 carbons (preferred is about 18 as exemplified by 2-octadecenyl); whereas, for applications as a dispersant or detergent in lubricants it is preferred that the hydrocarbyl substituents number from about 30 to 49 carbons, e.g. 35 to 45 carbons.

Both the chemical structure and number of the oxazoline rings have an influence on the functionality of the additive compounds of the invention. The bis oxazoline additive wherein THAM was the amino alkanol appears of highest efficacy in its anti-rust properties.

In summary, effective additives for oleaginous compositions can be prepared by reaction of a hydrocarbon substituted dicarboxylic acid material with a 2,2-disubstituted-2amino-1-alkanol under conditions such that formation of simple esters, imides or amides is eliminated, or at least minimized, so that a substantial proportion of the aminoalkanol is converted into oxazoline rings. Infrared spectrum on some of the aforesaid Examples indicate that a major proportion, and in some cases essentially all, of the aminoalkanol was converted to oxazoline rings.

The invention in its broader aspect is not limited to the specific details shown and described and departures may be made from such details without departing from the principles of the invention and without sacrificing its chief advantages.

What is claimed is:

1. A lubricating oil composition comprising: a major amount of lubricating oil and 0.1 to 10 wt. % of bis-oxazoline of a molar proportion of a hydrocarbon-substituted $C_4$-$C_{10}$ mono unsaturated dicarboxylic acid material selected from the group consisting of dicarboxylic acid, ester and anhydrides thereof, having from about 8 to 49 carbon atoms in said hyrocarbon substituent; reacted with about two molar proportions of a 2,2-disubstituted-2-amino-1-alkanol having 2 to 3 hydroxy groups and containing a total of 4 to 8 carbons of the formula:

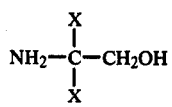

wherein X is alkyl or hydroxy alkyl, said alkyl groups having 1 to 3 carbon atoms, and at least one of said X is a hydroxy alkyl group of the structure —$(CH_2)_nOH$ where n is 1 to 3; at a temperature in the range of about 140 to 240° C. for about ½ to 24 hours with the removal of about three molar proportions of water to thereby produce said bis-oxazoline having the structure

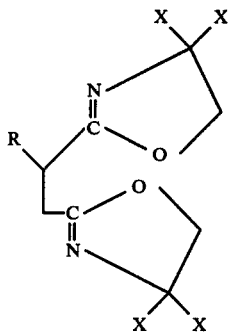

wherein R is said hydrocarbon substituent and X is as defined above.

2. A composition according to claim 1, wherein said hydrocarbon-substituted dicarboxylic acid material is alkenyl succinic anhydride.

3. A composition according to claim 2, wherein said amino-1-alkanol is 2-amino-2-methyl-1propanol.

4. A composition according to claim 2, wherein said amino-1-alkanol is tris-hydroxy-methylaminomethane.

5. A composition according to claim 1, wherein said time is about 2 to 8 hours.

6. An additive concentrate comprising: a major amount of mineral lubricating oil in the range of 98 to 45 parts by weight, 2 to 45 parts by weight of bisoxazoline of a molar proportion of a hydrocarbon-substituted $C_4-C_{10}$ mono unsaturated dicarboxylic acid material selected from the group consisting of dicarboxylic acid, ester and anhyrides thereof; having from about 8 to 49 carbon atoms in said hydrocarbon substituent; reacted with about two molar proportions of a 2,2-disubstituted-2-amino-1-alkanol having 2 to 3 hydroxy groups and containing a total of 4 to 8 carbons of the formula:

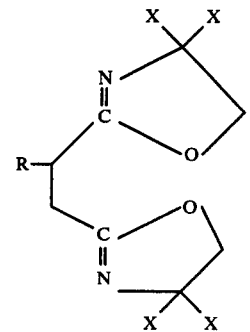

wherein X is alkyl or hydroxy alkyl, said alkyl groups having 1 to 3 carbon atoms, and at least one of said X is a hydroxy alkyl group of the structure —$(CH_2)_nOH$ where n is 1 to 3; at a temperature in the range of about 140° to 240° C. for about ½ to 24 hours with the removal of about three molar proportions of water to thereby produce said bis-oxazoline having the structure wherein R is said hydrocarbon substituent and X is as defined above.

7. A concentrate according to claim 6, wherein said hydrocarbon substituted dicarboxylic acid is alkenyl succinic anhyride.

8. A concentrate according to claim 7, wherein said amino alcohol is 2-amino-2-methyl-1-propanol.

9. A composition according to claim 7, wherein said amino alcohol is tris-hydroxy-methylaminomethane.

10. A composition according to claim 6, wherein said temperature is about 170° to 220° C. and said time is about 2 to 8 hours.

* * * * *